March 22, 1955
VINCENZO SODANO
KNOWN AS
JIMMY SODANO
ROSE PLANT
Filed March 9, 1954
Plant Pat. 1,364
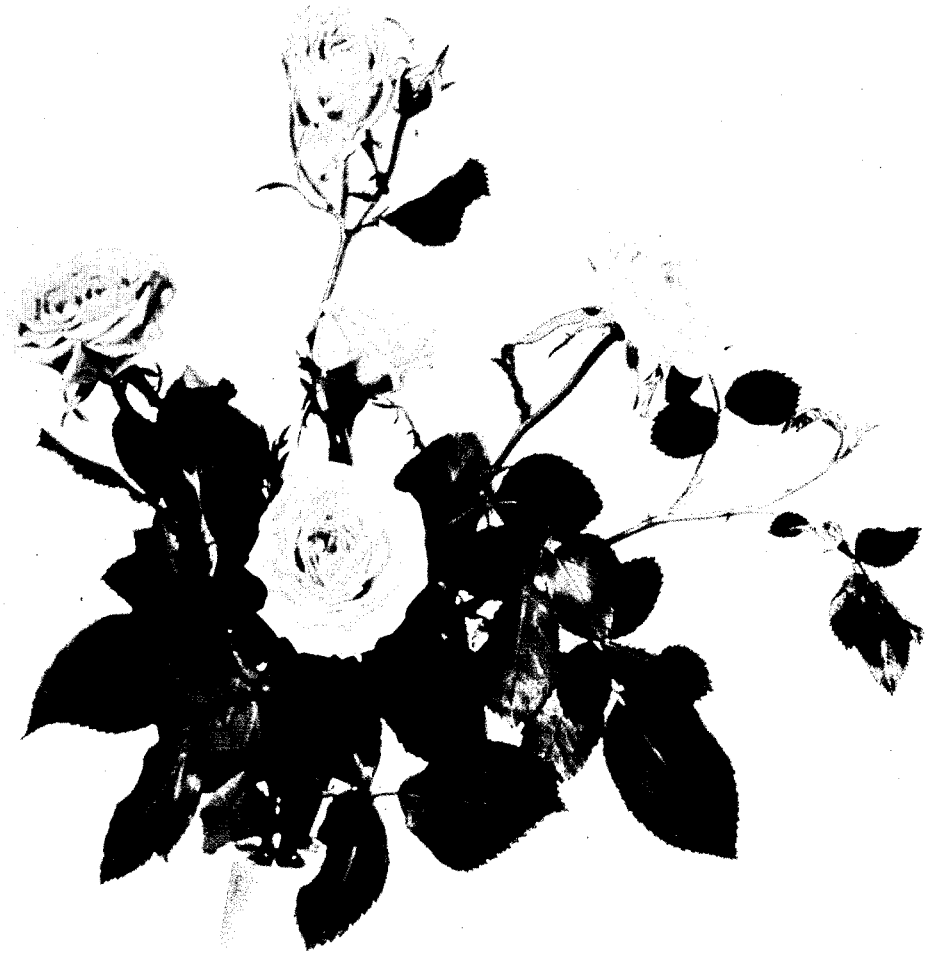
INVENTOR
Vincenzo Sodano
Also Known as Jimmy Sodano
By Orville M. Kile
Plant Patent Agt.

United States Patent Office

Plant Pat. 1,364
Patented Mar. 22, 1955

1,364

ROSE PLANT

Vincenzo Sodano, known as Jimmy Sodano, Madison, N. J.

Application March 9, 1954, Serial No. 415,186

1 Claim. (Cl. 47—61)

My present discovery pertains to a new and distinct variety of rose plant of the polyantha type, which originated as a pink sport of the variety Garnette (unpatented) in my greenhouses in Madison, N. J.

My new variety is similar to its parent in many respects but differs principally in its higher and more vigorous growth, and its flowers of larger petalage, different color, longer stem and better lasting qualities.

I have asexually reproduced my new variety at my greenhouses, by means of budding, and its distinguishing features appear to be permanently fixed.

Accompanying illustration shows a bunch of roses in various stages of opening, together with portions of stems and both old and new foliage—all in approximately true colors, although there is some apparent variation because of highlights.

Following is a detailed description of my new variety. Color plate numbers refer to Ridgway's Color Standards and Nomenclature, while other reference to color indicates the dictionary meaning.

THE PLANT

Growth: Plant grows freely and vigorously, attaining a height of 4 or 5 feet. Heavily wooded.

Blooming habits: Blooms continuously and profusely.

Stems: Thick and straight with few and scattered thorns. Color between Oil Green and Spinach Green (both Plate V).

Foliage:

*Quantity.*—Abundant.

*Type.*—Three to five leaflets.

*Leaves*:

Size—Leaves approximately 2½ inches long and 1½ inches wide, with terminal leaflet measuring about 1½ by 2 inches.

Shape—Broad ovate, with rounded base and pointed apex.

Texture—Heavy.

Color—Approximately Forest Green (Pl. XVII) with new foliage red-tinged, approximately Vinaceous-Russet (Pl. XXVIII).

Rachis—Slender, reddish-tinged on upper surface; lower surface green. Sometimes thornless but frequently with 1 to 3 small thorns on under side.

Stipules—Adnate; slender. Points measure approximately one-fourth inch long.

THE BLOOM

Bud:

*Form.*—Short; stocky, although hooded calyx gives effect of being pointed.

*Size.*—Small. As calyx breaks it is approximately ⅝ to ¾ inch long.

*Sepals.*—Of the five, usually two are simple, with three branching and measuring 1 to 1½ inch long.

*Color.*—Deep Rose Pink (Pl. XII).

*Peduncle.*—Strong and long for this type rose. Cut flower stem measures approximately 16 inches.

Flower:

*Size.*—Two inches in diameter when fully opened.

*Form.*—Very full, with slightly depressed center. Opens to deep cupshape. Stamens usually visible in the fully opened flower.

*Color.*—Specimens vary from Deep Rose Pink to a color almost Rose Color (both Pl. XII), but typical specimens have a color which falls between Deep Rose Pink and Rose Color deep in the center, with the outer several rows approximately Rose Pink (Pl. XII). The reverse of the petals is lighter in tone and each petal has a large white aiglet.

*Petalage.*—Varies from 50 to 75 petals, with 65 to 70 the average for the Fall season.

*Fragrance.*—Distinct rose odor, somewhat like that of a garden rose.

*Longevity.*—Exceptionally long-lasting. A number of tests have shown cut flowers at usual room temperatures to last 2 to 2½ weeks. It has not been determined how long the flowers last on the plant but some have lasted for over 3 weeks.

Petals:

*Size.*—Outer petals are from ¾ to 1 inch long and slightly narrower. Inner petals are progressively smaller and narrower toward center of the flower.

*Shape.*—Outer petals cupped and slightly reflexed. Edge of outer petals wavy and sometimes notched, but inner petals are straighter edged.

*Arrangement.*—Imbricated.

*Texture.*—Very delicate; a satin finish to the touch.

Reproductive organs:

*Pistils.*—Several; bunched in center of flower.

Styles—Short in center, with slightly longer outer circle; rise higher than stamens; partly enclosed in calyx.

Stigmas—Yellow-beige, approximately Light Greenish Yellow (Pl. V).

*Stamens.*—Fewer than pistils, and surrounding them.

Filaments—Short to very short, the longest being about ⅝ inch.

Anthers—Medium size. Pale yellow to brown but mostly approximately Apricot Yellow (Pl. IV).

COMPARISON

The rose variety known to me which is most like my new variety is the subject of Plant Patent No. 1232, which is also a pink sport of Garnette. The principal differences are as follows:

1. The growth of the plant of my new variety is much more vigorous and the plant becomes at least twice as tall.
2. The leaflets and foliage of my variety are larger.
3. The stems of my variety are straight rather than the zigzag type of the stems of Plant Patent No. 1232.
4. The peduncle of my flower is longer, permitting longer stems for cut flowers.
5. The bud of my variety is smaller when color first shows.
6. The flower of my variety is deeper-cupped, the outer petals being a little longer and more curved.
7. The flower of my variety is fuller-petaled, allowing it to open and unfurl to resemble shells.
8. The flower of my variety has a deeper shade of pink, particularly when open, and the color does not fade.
9. Fragrance of the flower of my variety is more distinct.
10. The flower of my variety lasts longer, both as a cut flower and on the bush.
11. Reproductive organs differ in that the pistils of the flower of my new variety rise above the stamens, while in Plant Patent No. 1232 the stamens are the longer and are curved.

Having thus disclosed my discovery, I claim:

The new and distinct polyantha rose plant substantially as herein shown and described, characterized particularly by its tall and vigorous growth; its straight sturdy stems; its long peduncle; and its full-petaled, fragrant flower with unfading pink color, deep cupshape, and exceptionally long-lasting quality.

No references cited.